(12) United States Patent
Smorgon (10) Patent No.: US 10,302,575 B2
(45) Date of Patent: May 28, 2019

(54) INTRAOCULAR LENS INSPECTION

(71) Applicant: EMAGE VISION PTE. LTD., Singapore (SG)

(72) Inventor: Sergey Smorgon, Singapore (SG)

(73) Assignee: EMAGE VISION PTE. LTD., Singapore (SG)

(*) Notice: Subject to any disclaimer, the term of this patent is extended or adjusted under 35 U.S.C. 154(b) by 0 days.

(21) Appl. No.: 15/962,708

(22) Filed: Apr. 25, 2018

(65) Prior Publication Data

US 2018/0306732 A1    Oct. 25, 2018

(30) Foreign Application Priority Data

Apr. 25, 2017  (SG) .............. 10201703345R (51) Int. Cl.
*G01N 21/958*  (2006.01)
*A61F 2/16*    (2006.01)
*G01N 21/88*   (2006.01)

(52) U.S. Cl.
CPC .............. *G01N 21/958* (2013.01); *A61F 2/16* (2013.01); *G01N 21/8806* (2013.01); *G01N 2021/8822* (2013.01); *G01N 2021/9583* (2013.01)

(58) Field of Classification Search
CPC ....... G01N 21/9501; G01N 2021/8822; G01N 21/8806; G01N 21/94; G01N 21/95607; G01N 21/95623; G01N 21/956; G01N 21/958; G01N 21/95684; G01N 2021/8848; G01N 21/21; G01N 21/47; G01N 2201/06113; G01N 2201/063; G01N 2021/4711; G01N 2021/9583; G01N 2021/8825; G01N 2021/95615; G01N 21/03; G01N 21/8803; G01N 21/8851; G01N 2201/0618; G01N 2201/0634; G01N 21/33; G01N 21/59; G01N 21/90; G01N 21/9018; G01N 21/9036; G01N 2201/0697; G01N 2223/418; G01N 2223/6466; G01N 2223/66; G01N 23/2251; G01N 2021/217; G01N 2021/8472; G01N 2021/8835; G01N 2021/8841; G01N 2021/8887; G01N 2021/9513; G01N 21/474; G01N 21/55; G01N 21/896; G01N 2201/0636; G01N 2201/12; G01M 11/0278; G01M 11/0214;
(Continued)

(56) References Cited

U.S. PATENT DOCUMENTS 6,198,529 B1 *  3/2001  Clark, Jr. ......... G01N 21/95684
                                                   356/237.5
6,201,600 B1 *  3/2001  Sites ................. G01M 11/0264
                                                   356/124

(Continued)

*Primary Examiner* — Michael P Stafira
(74) *Attorney, Agent, or Firm* — Mannava & Kang, P.C.

(57) ABSTRACT

An inspection system and method to inspect for defects in molding, contamination, scratches, damage and any form of deformation in intraocular lens comprising three main building blocks; a Top illumination light head that includes a Top lens light head and a Top flat light head; a Dark field illumination light head, a Bright field illumination light head; a Single spot illumination light head; a image acquisition and processing system which captures images of the lens loaded in trays; analyzing the image to detect the various defects; making a conclusion to reject or accept the lens, based on the analyzed image.

8 Claims, 5 Drawing Sheets

(58) Field of Classification Search
CPC .............. G01M 11/02; G01M 11/0207; G01M 11/0257; G01M 11/0285; G02B 21/0016; G02B 1/041; G02B 21/26; G02B 21/362; G02B 21/367; G02B 26/02; G02B 13/143; G02B 17/0808; G02B 17/0856; G02B 17/0892; G02B 21/16; G02B 27/141; G02B 6/0008; G02B 6/4298; G01B 11/255
See application file for complete search history.

(56) References Cited

U.S. PATENT DOCUMENTS

| | | | |
|---|---|---|---|
| 6,301,005 B1* | 10/2001 | Epstein | G01M 11/0278 356/124 |
| 2002/0122172 A1* | 9/2002 | Ross, III | G01B 11/255 356/124 |
| 2006/0012778 A1* | 1/2006 | Vaughnn | G01N 21/8806 356/237.2 |
| 2017/0011507 A1* | 1/2017 | Wong | G01N 21/896 |

* cited by examiner

Dark field illumination

Fig 5

Bright field illumination

INTRAOCULAR LENS INSPECTION

PRIORITY

The present application claims priority under 35 U.S.C. 119(a)-(d) to Singaporean patent application number 10201703345R, having a filing date of Apr. 25, 2017, the disclosure of which is hereby incorporated by reference in its entirety.

FIELD OF THE INVENTION

The present invention relates to an apparatus and method for detecting defects in intraocular lenses loaded in trays, using multiple illumination modules. More specifically, the present invention relates to an apparatus and method to detect damage, aberrations, contamination, deformation & geometrical properties in intraocular lenses.

BACKGROUND OF THE INVENTION

The present invention relates to an inspection system in the quality assurance process either in the form of sample inspection or as part of an automated production line. More particularly, the invention relates to a system and method of inspection of intraocular lens that are transported in trays. Intraocular lens are implanted into the eye to correct and stabilize the vision of patients immediately after a cataract operation. As the process is permanent, the quality of the lens embedded in the eye needs to be reliably and accurately inspected for quality that includes dimensions, surface defects and other edge related defects.

Manufacturers generally adopt manual inspection by using optical scopes with large magnification. These methods are tedious and some of the defects may not be discernible to the human eye, leading to defective lens reaching the customer. Moreover, it is unreliable & tedious to perform manual inspection on every lens that is shipped.

It is generally understood that a well-designed automated inspection system is required as they are accurate, consistent and easily configured for different product types with little human intervention.

A single apparatus and method utilizing LED illumination modules, that can produce accurate and reliable images of lenses loaded in a tray, to enable inspection of multiple features such edge defects, geometrical measurements, contamination, is the objective of the present invention.

SUMMARY OF INVENTION

An intraocular lens henceforth also referred to as IOL, is a surgical implant used to replace the lens within an eye, where the lens has been removed, for intraocular lens example, as a result of cataract surgery, disease, or physical damage.

During the manufacturing process the Intraocular lenses may be subject to a variety of defects. The following list defines various typical defects, although the terminology may vary from one manufacturer to another.

Scratches: Scratches appear as long, narrow surface abrasions.

Digs: Digs are crater-like surface defects usually with a length/width ratio of approximately 1. This type of defect can occur anywhere on the surface of the IOL.

Pits: Pits are surface defects with a length/width ratio of approximately 1. The defect is characterized by a lack of IOL material and occurs inward into the IOL surface. Surface contour changes associated with the defect are typically gradual and smooth.

Voids: Voids are defined in areas generally near the edge of an IOL, where a portion of the IOL is missing. Voids form during the IOL molding process when material does not completely fill the mold.

Tears: Tears appear as small rips along the edge of the IOL. Tears can occur at any location along the edge of the lens between the optic edge and the loop.

Bubbles: Bubbles are internal voids that can occur any where in the one-piece IOL and only in the optic zone of the three-piece IOL. Bubbles are the result of air pockets present in the IOL material when injected into the mold during manufacture.

Loop damage: Loop damage is classified as any kind of damage or malformation of a loop applicable to lens with loops only. The most prevalent type of loop damage include smashed anchors, smashed loops, missing loops and tweezer damage.

Edge flash: Edge flash appears as flakes of IOL material attached to the edge of an IOL or as a thin coating covering the surface of loops. Edge flash is the result of excess IOL material flowing out of the mold during manufacture.

Foreign Material: They are defined as small particles adhering to the surface of an IOL that cannot be removed by cleaning. A substance many times appears as fine mist that causes the IOL to have an unusual tint.

Uncured: Uncured material primarily occurs near the edge of the optic zone in one-piece IOLs. Uncured material appears as a jelly-like substance on the perimeter of an IOL. This defect develops during the lens curing process due to incorrect heating times or non-uniform heating.

Mold Flow marks: They appear as uneven seams or unusual surface contours in the optic or loop zone. Flow marks typically form as long, thin defects that follow a smoothly winding direction, or path. Flow marks occur during the molding process when the IOL material cures before flowing is completed.

An intraocular lens inspection system to inspect most of the defects described earlier, is provided in accordance with the present invention which comprises a lens image acquisition block comprising a high resolution camera, a telecentric lens arranged to view the image of the lens through a beam splitter, at least three sets of lighting modules designed using LEDs in the visible spectrum of light, to illuminate the lens under inspection, the first one being a Top light head module herein referred to as the Topside Light head, comprising at least two light heads, one of which illuminates the lens right angles to the optical axis of the lens and the other illuminating the lens at an angle to the top surface of the lens, a second illumination module herein referred to as the Backside Light head, comprising at least three lighting modules herein referred to as Dark Field Light head, Bright Field Light head and Single Spot Light head integrated and suitably arranged with a set of beam splitters to illuminate the lens under inspection. The Dark field light head illuminates the bottom of the lens to produce a Dark field image of the lens, a second lighting module namely the Bright field light head illuminates the lens to produce a bright field image of the lens and the Single Spot light head illuminates the lens with a narrow beam of light at right angle to the surface of the lens. The single spot light head is integrated with a motor primarily to position the Single spot light head at different positions based on the optical power of the intraocular lens. Furthermore, an electronic strobing system is integrated into the inspection system to control the intensity, duration and timing of the individual illumination modules in sync with the camera shutter to capture images under different lighting conditions.

The intraocular lens inspection system acquires multiple images of the object under different illumination configurations to enhance the features of the lens under inspection.

It is an object of the present invention to provide an apparatus and method for inspecting the intraocular lens positioned in a tray by acquiring multiple images, using multiple illumination configurations, depending upon the product type.

It is further an object of the present invention to provide an apparatus and method to provide product configurations stored in recipe files which may include illumination intensities, camera shutter timing and duration, motor position of the Single spot light head among others, based on product types that are downloaded during the setup of the inspection system.

It is further an object of the present invention to provide an apparatus that is integrated with a strobe controller, capable of electronically triggering multiple illumination modules with short trigger pulses at any given instance, synchronously or asynchronously based on the software program.

Other features and objects of the present invention will become apparent from the detailed description of the preferred embodiment(s) as well as the drawing figures included herein below.

BRIEF DESCRIPTION OF DRAWINGS

It will be convenient to further describe the present invention with respect to the accompanying drawings that illustrate possible arrangements of the invention. Person skilled in the art will appreciate that other arrangements of the invention are possible, and consequently the particularity of the accompanying drawings is not to be understood as superseding the generality of the preceding description of the invention.

DETAILED DESCRIPTION OF THE PREFERRED EMBODIMENT(S)

Although the invention is applicable to various types of optically transmissive components, it will be described by way of example with respect to those having a lens portion, and more particularly to IOLs Referring to FIG. 1, and in accordance with a constructed embodiment of the present invention, a system 100 is illustrated that analyzes and detect damage, aberrations, contamination, deformation & geometrical properties, which includes three main modules 101, 102 & 103. The Top side illumination module 101, the Back light illumination module 103 & the image acquisition module 102.

The Top side illumination module 101 comprises two types of LED light heads, the Top lens light head 14 & the Top Flat light head 10. The Top light head 14 comprises the illumination light head 16 and a lens 18 to direct the light towards the sample contained in the tray 22. The Top flat light head 10 is arranged to illuminate the sample in tray 22 at an angle.

The Back light illumination module 103 comprises three illumination modules. The Dark field illumination module 34, The Bright Field illumination module 36 & the Single Spot illumination Module 30. The lens 24 directs all three types of illumination to the bottom surface of the sample held in the component carrier 22. The Single Spot illumination module 30 is positioned by a motor 38 depending upon the optical power of the lens being inspected in the tray. The position of illumination module is pre-determined based on the model of the lens to be inspected, during configuration setup and stored in recipes. The lens 32 is used to focus the light from the single spot illumination 30. Beam splitters 26 and 28 together form a beam splitter block that are utilized to redirect the illumination from three illumination modules 30, 34 and 36, towards the lens 24.

The image acquisition module 102 comprises a high resolution camera 11, a telecentric lens 12 and a beam splitter 20 to direct the illumination from all the different illumination configurations. The image acquisition module is controlled by an image processing computer (not shown) and the illumination modules 10, 14, 34, 36 and 30 are triggered asynchronously by an electronic strober (not shown). The strober is also programmed to trigger the illumination modules in sync with the camera shutter to capture images under different illumination configurations. The software program determines the timing of the camera shutter and the trigger to the illumination modules to capture images of the sample.

In accordance with another embodiment of the present invention, the illumination modules 10, 14, 34, 36 and 30 may be triggered at different intensities, depending upon the type of sample & features being inspected.

In accordance with another embodiment of the present invention, the illumination modules 10, 14, 34, 36 and 30 may be dynamically configured in form of segments in such a way that only the selected segments in the Light heads will illuminate based on the configuration that was stored in recipe files during setup.

In accordance with another embodiment of the present invention, the illumination module 30 and lens 32 may be dynamically positioned based on different product types of the lens to be inspected, wherein the positions may be stored in recipe files during setup.

Top side illumination block work with on two methods—light reflection and light scattering. It allows to get images based on reflected light (TopLens LH) and scattered light (TopFlat LH). Top Lens LH include the LEDs holder and top lens. Top Flat LH include the LEDs holder and diffuser.

Figure 2:
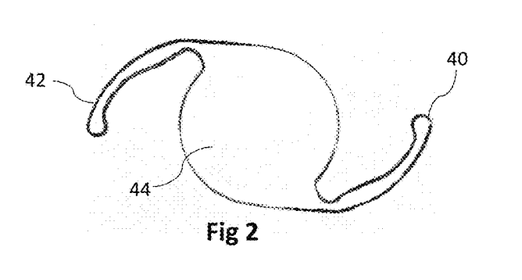
FIG. 2 is an illustration of one type of intraocular lens with 44 being the optic zone and includes loops 42 and 40 for surgical connection to the eye. The loops 40 and 42 is secured to the optic zone 44.

FIG. 2 illustrates a drawing of an intraocular lens. Loops 40 and 42 are at opposite sides of the optical zone 44 of the lens.

Figure 3:
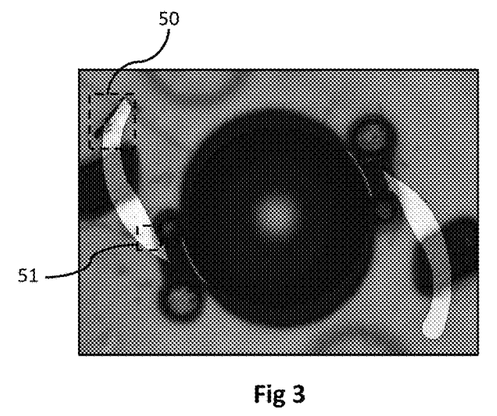
FIG. 3 illustrates an image of an intraocular lens positioned in a tray captured with the system of the present invention in FIG. 1, illuminated by the Top Lens Light head.
Figure 3A:
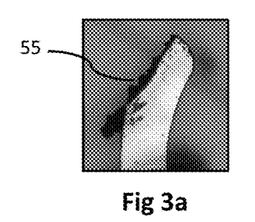
FIG. 3a illustrates an enlarged image of area 50 in FIG. 3
Figure 3B:
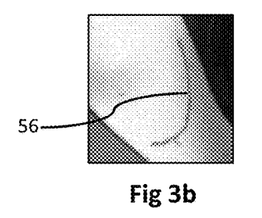
FIG. 3b illustrates an enlarged image of area 51 in FIG. 3

FIG. 3 illustrates an image of the intraocular lens captured utilizing the Top side illumination. The configuration of the Top side illumination 14 is configured to reflect light from the flat surface for the intraocular lens so as to enhance certain effectively. FIG. 3a is an enlarged image of area 50 in FIG. 3 and FIG. 3b is an enlarged image of area 51 in FIG. 3. In FIG. 3a, damage is evident as shown at 55 and in FIG. 3b, contamination is observed at 56. The incident light reflecting from the top surface of the loops 40 and 42 in FIG. 1, produces an optimum image that highlights defects such as contamination and lens damage effectively.

Figure 4:
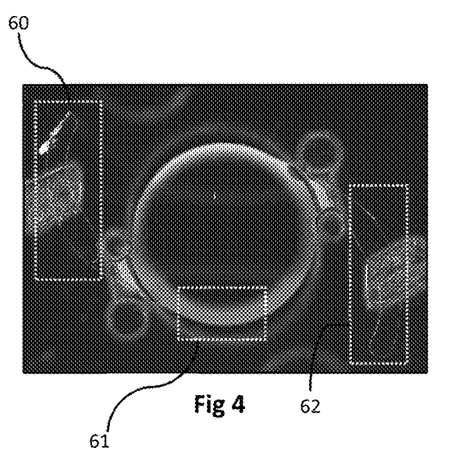
FIG. 4 illustrates an image of an intraocular lens positioned in a tray captured with the system of the present invention in FIG. 1, illuminated by the Top Flat Light head.
Figure 4A:
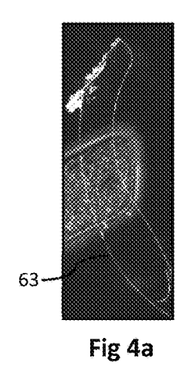
FIG. 4a illustrates an enlarged image of area 60 in FIG. 4.
Figure 4B:
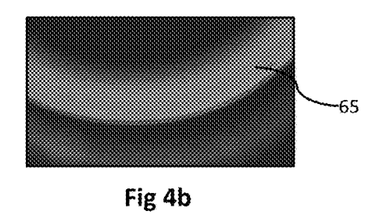
FIG. 4b illustrates an enlarged image of area 61 in FIG. 4.
Figure 4C:
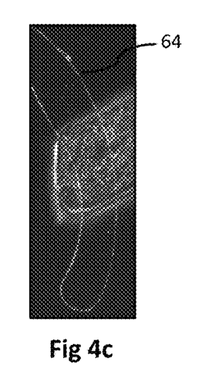
FIG. 4c illustrates an enlarged image of area 62 in FIG. 4.

As the optical zone 44 is curved, good reflection is not observed in this area when Top side illumination 14 is used. Moreover the edges of the lens as illustrated in FIG. 3 is not clear and any measurements of the dimensions of the loops and the lens size may not be accurate. To enhance the edges of the lens, the Top side Flat light head 10 is utilized. FIG. 4 illustrates an image of the intraocular lens captured using the Top side Flat light 10. The configuration of the Top side flat illumination 10 is configured to illuminate the lens at an angle to enhance the edges effectively. FIG. 4a is an enlarged image of area 60 in FIG. 4 and FIG. 4b is an enlarged image of area 61 in FIG. 4. In FIG. 4a & FIG. 4c, the edges of lens is evidently clear with good contrast, as observed at 63 and 64 respectively. Dimensions such as width, length and distance of the loop from the center of the optical zone are some of the key measurements that can be analyzed from the image FIG. 4. A person skilled in the art will realize that other dimensions can also be measured in image FIG. 4, based on customer requirements. FIG. 4c is an enlarged image of area 62 in FIG. 4. It may be observed that the area 65 around the lens has a bright band whose width is a direct relation of the curvature of the lens. The width of area 65 in FIG. 4b around the lens, can vary depending upon on the optical curvature of the intraocular lens. The optical zone curvature is therefore easily measured and correlated with the power of the Intraocular lens, enabling the inspection system to isolate or reject lenses with different curvatures or optical power.

Figure 1:
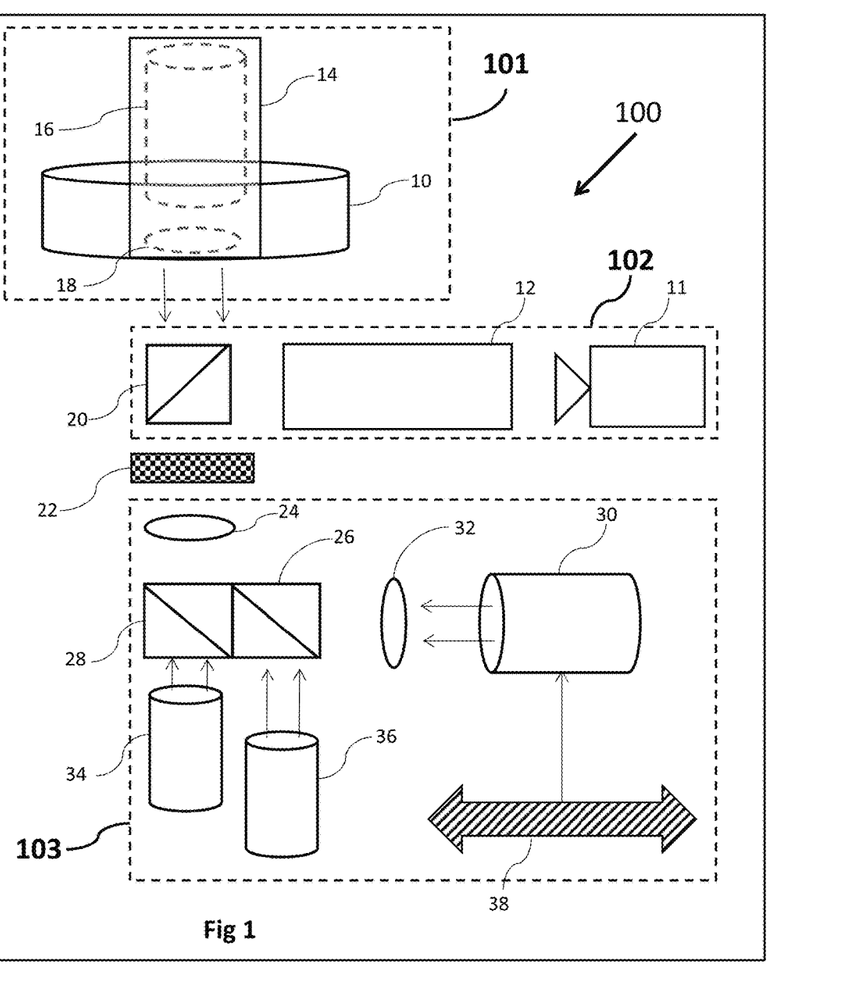
FIG. 1 is an illustration of the optical, illumination and imaging system according to the present invention.
Figure 5:
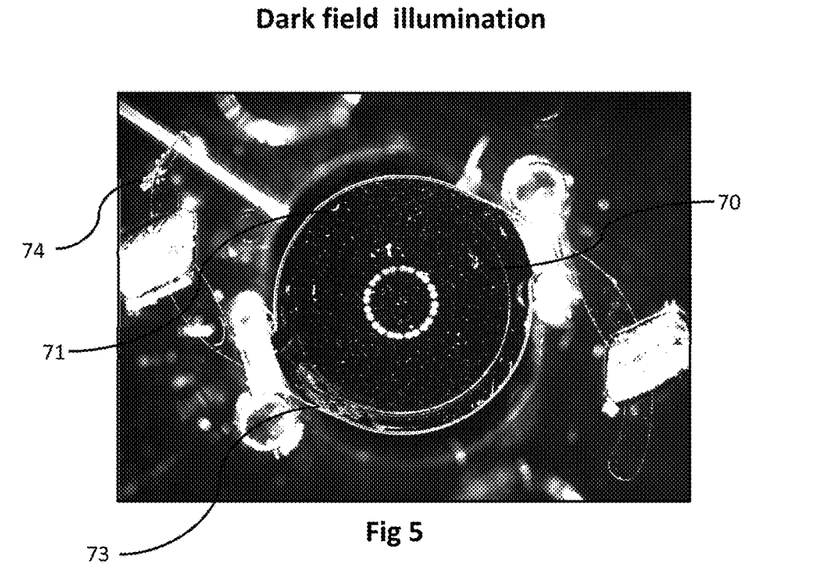
FIG. 5 illustrates an image of an intraocular lens positioned in a tray captured with the system of the present invention in FIG. 1, illuminated by the Dark Field light head.

FIG. 5 is an image of the Intraocular with the Dark Field illumination light head 34 shown in FIG. 1. The Dark Field light head features a specially treated surface that absorbs all reflected light from the sample, resulting in a high contrast image as shown in FIG. 5. The Dark field illumination is configured to produce narrow beam of light which is incident on the surface of the lens at 45 degrees to the optical axis. The image captured under Dark field illumination configuration enhances defects related to contamination, deformation in the optical zone & excess mold flash. In FIGS. 5, 70 and 71 shows contamination defects and 73 indicates possible deformation in the optical curvature area. Mold flash or damage can also be observed at 74 in FIG. 5. The important point to note here is that defects with the use of Dark field illumination module 34 as shown in FIG. 1, features are highlighted from the bottom and top surface of the lens making the inspection more efficient and robust.

Figure 5A:
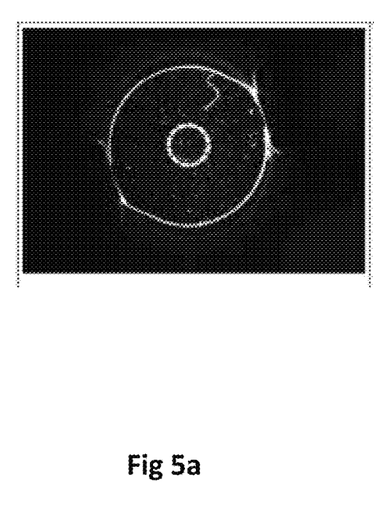
FIG. 5a illustrates a full ring DF image of FIG. 5.
Figure 5B:
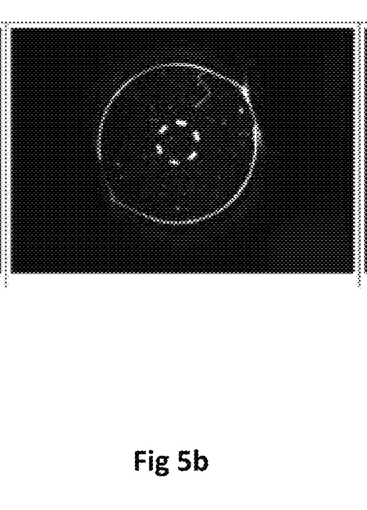
FIG. 5b illustrates a bit 1 DF image of FIG. 5.
Figure 5C:
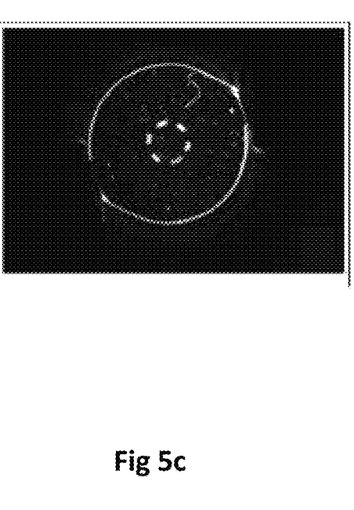
FIG. 5c illustrates a bit 2 DF image of FIG. 5.

With the full ring DF illumination as shown in FIG. 5 can see all defects with good contrast, but also visible lighting configuration. It happened because two times reflection on both surfaces of optical zone. DF LH divided for 2 bits to be able to do inspection in area of LH bright spots. FIGS. 5a, 5b and 5c are three images with DF illumination can be done if necessary to have full optical zone inspection. But practically full ring image is good enough as we have other images where area covered by bright spots can be tested.

Figure 6:
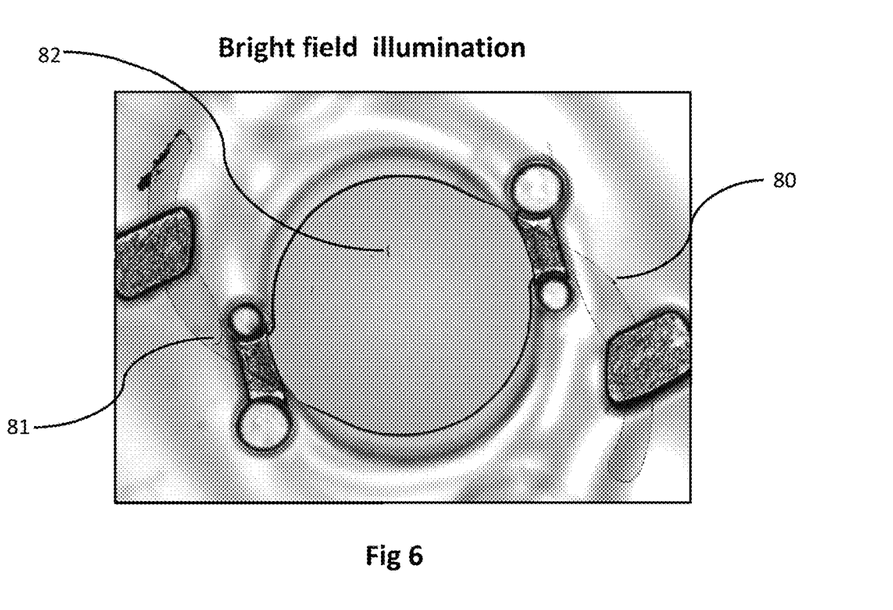
FIG. 6 illustrates an image of an intraocular lens positioned in a tray captured with the system of the present invention in FIG. 1, illuminated by the Bright Field light head.

FIG. 6 is an image of the intraocular with the Bright Field illumination light head 36 shown in FIG. 1. The Bright field illumination module 36 is configured to produce light which is incident on the surface of the lens at a very wide angle to the optical axis. Bright field light head forms light with a wide angular aperture of illumination. The image captured under Bright field illumination configuration enables geometrical measurements such as lens size and position of the lens. In addition certain gross contamination defects indicated by 80, 81 and 82 indicated in FIG. 6, is optimally enhanced that aids in easy detection of defects.

Figure 7:
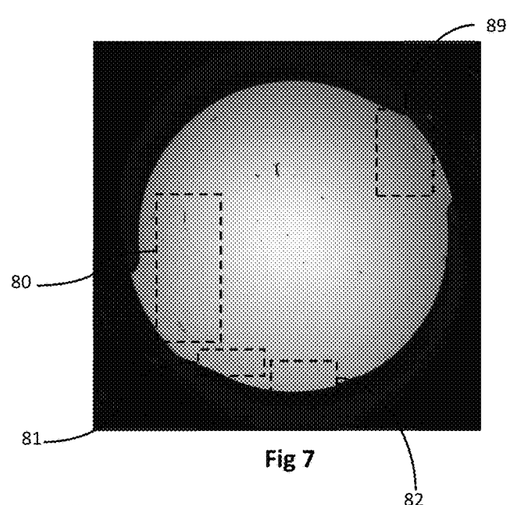
FIG. 7 illustrates an image of an intraocular lens positioned in a tray captured with the system of the present invention in FIG. 1, illuminated by the Single Spot light head.

FIG. 7 is an image of the intraocular with the Single spot illumination light head 30 shown in FIG. 1. The illumination from 30 is further focused to produce a narrow beam of light using lens 32 which is differently positioned to adjust the illumination to suit the type of lens to be inspected. Single spot light head is intended to form narrow beams of light arriving at the sample surface at right angles (about 0 degrees to the optical axis). Optics of elements also included into light refraction for SS image. As result for different optical power elements position of SS light source must be different. So SS LH consist SS lens, SS Led, stepping motor. With this stepping motor we can choose correct position of SS light head for samples with different optical power. It's the best image for optical zone inspection. But the other portions of object not visible under such illumination method.

Most defects of optical zone has good contrast under SS illumination method. DF need for defects with low SS contrast. BF is useful for position and dimension. Top Flat need for edge defects. TopLens can detect all flat areas. With combination of all 5 methods can detect almost 100% defects.

The mechanism of adjustment is attained by suitably integrating the illumination light head 30 and lens 32 to a motor 38. The movement of the motor is controlled by a computer and the position is determined during setup and configuration of the illumination and stored in recipe files which may be downloaded during the inspection process. The image captured under Single shot illumination configuration enables detection of defects such as surface deformation, scratches, contamination, and defect generally known as the orange peel.

Figure 7A:
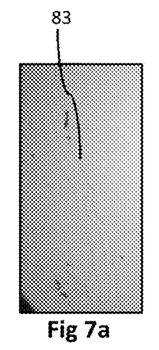
FIG. 7a illustrates an enlarged image of area 80 in FIG. 7.
Figures 7B, 7D:
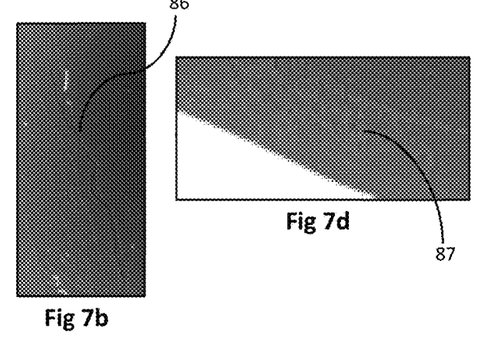
FIG. 7b illustrates a processed image of area 80 in FIG. 7.
FIG. 7d illustrates a processed image of area 81 in FIG. 7.
Figure 7C:
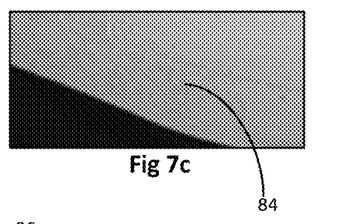
FIG. 7c illustrates an enlarged image of area 81 in FIG. 7.
Figure 7E:
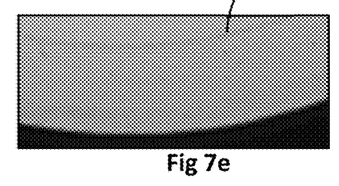
FIG. 7e illustrates an enlarged image of area 82 in FIG. 7.
Figure 7F:
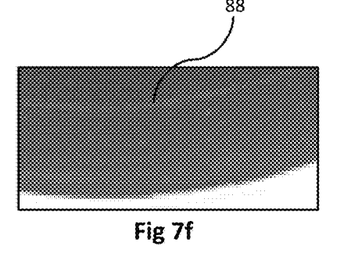
FIG. 7f illustrates a processed image of area 82 in FIG. 7.
Figure 7G:
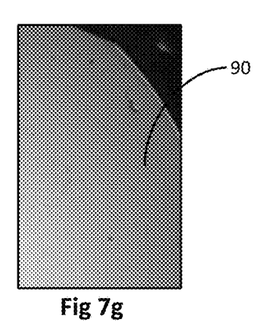
FIG. 7g illustrates an enlarged image of area 89 in FIG. 7.
Figure 7H:
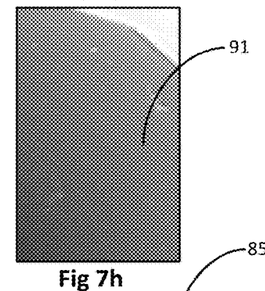
FIG. 7h illustrates a processed image of area 89 in FIG. 7.

FIG. 7a is an enlarged image of area 80 in FIG. 7. FIG. 7b is a processed image of area 80 in FIG. 7. The surface deformation in the optical area is clearly visible at 83 and 86 of FIGS. 7a and 7b respectively. FIG. 7c is an enlarged image of area 81 in FIG. 7. FIG. 7d is a processed image of area 81 in FIG. 7. The contamination is evident in the optical area at 84 and 87 of FIGS. 7c and 7d respectively. FIG. 7e is an enlarged image of area 82 in FIG. 7. FIG. 7f is a processed image of area 82 in FIG. 7. The scratch is highlighted at 85 and 88 of FIGS. 7e and 7f respectively. FIG. 7g is an enlarged image of area 89 in FIG. 7. FIG. 7h is a processed image of area 89 in FIG. 7. The concentric lines on the surface of the optical area commonly referred to as the orange peel defect, may be observed at 90 and 91 of FIG. 7g and FIG. 7h respectively. The Single spot illumination light head integrated with the Single Spot lens and the motorised position mechanism, provides an enhanced system and method to inspect for various surface defects of the lens.

Modifications to the present invention in its various embodiment(s) will become obvious to those skilled in the art upon reading this disclosure and may be made without departing from scope of the invention encompassed by the claims appended hereto. In view of the above, it will be seen that the several objectives of the invention are achieved and other advantages are obtained. As many changes could be made in the above constructions and methods without departing from the scope of the invention, it is intended that all matter contained in the above description shall be interpreted as illustrative and not in a limiting sense.

The invention claimed is:

1. An inspection device for inspecting an intraocular lens, the device comprising:
   an image acquisition module comprising a high resolution camera, a customized telecentric lens and focusing mechanism that is arranged to capture an image of said intraocular lens;
   a first bright field illumination module, the bright field illumination module comprising a first light source directed to the top surface of the lens enabling image capture of reflected light from the surface of the lens loops which have a flat surface;
   a second bright field illumination module, the bright field illumination module comprising a second light source directed to the top surface of the lens enabling image capture of scattered light from the optical surface and loops of the lens;
   a third bright field illumination module, the bright field illumination module comprising a third light source directed to a bottom surface of the lens at a very wide angle to the lens optical axis;
   a dark field illumination module, the dark field illumination module comprising a fourth light source arranged to be directed to the bottom surface of said lens, said fourth light source arranged to produce a narrow beam that is incident on the surface of the intraocular lens at 45 degrees to the optical axis;
   a single spot illumination module, the single spot illumination module comprising a narrow beam light source incident at right angles to the lens surface and a single spot lens suitably integrated to an electrically controlled dynamic positioner;
   a backlight front lens that configures the directions of all illumination rays originating from the back light illumination modules;
   wherein said light sources are arranged to enhance a specific defect on the optical curvature and the loop surface of said intraocular lens for image capture by said image acquisition module.

2. The inspection device according to claim 1, further including a top side illumination module, said top light illumination module comprising a top light source directed to the surface of said lens;
   wherein said top light source is arranged to highlight damage evident on said lens surface for capture by said image acquisition module.

3. The inspection device according to claim 1, further including a bright field illumination module, said bright field illumination module comprising a bright field light source directed at the curved surface of the intraocular lens, such that incident light is subsequently reflected at a wide angle to said lens;
   wherein an image captured of said reflected light permits the measurement of a geometric property of said lens.

4. The inspection device according to claim 1, wherein the top side illumination module includes a flat light head arranged to enhance edges of said lens, such that an image captured from reflected light from the flat light head provides geometric properties of loops associated with said intraocular lens.

5. The inspection device according to claim 1, wherein the single spot illumination module integrated with a focusing lens is mounted on a motor which is positioned at different points based on the optical power of the lens.

6. The inspection device according to claim 5, wherein the position of the single spot illumination module is determined through a pre-configured look up table based on the optical power of the lens.

7. The inspection device according to claim 1, wherein all illumination modules are suitably positioned to eliminate any interference during image capture.

8. The inspection device according to claim 1, wherein the top side illumination modules are suitably arranged to illuminate the lens located within transparent and translucent trays.

* * * * *